United States Patent [19]

Fancher

[11] Patent Number: 4,716,156
[45] Date of Patent: Dec. 29, 1987

[54] PHOSPHONODITHIOYLACETYL PHENYL AMINOACID ETHYL ESTERS

[75] Inventor: Llewellyn W. Fancher, New Castle, Calif.

[73] Assignee: Stauffer Chemical Co., Westport, Conn.

[21] Appl. No.: 296,286

[22] Filed: Aug. 26, 1981

[51] Int. Cl.⁴ .......................... A01N 57/02; C07F 9/40
[52] U.S. Cl. ...................................... 514/119; 558/174
[58] Field of Search .......................... 260/941; 424/211; 558/174; 514/119

[56] References Cited

U.S. PATENT DOCUMENTS 3,711,578 1/1973 Pianka .................................. 424/211
4,316,896 2/1982 Thorsett et al. ..................... 424/211

Primary Examiner—Anton H. Sutto
Attorney, Agent, or Firm—Michael J. Bradley

[57] ABSTRACT

Novel compounds having the formula

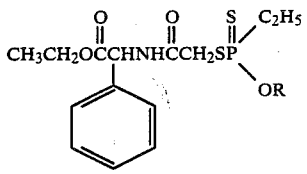

wherein R is lower alkyl having 1 to 6 carbon atoms, have shown utility as insecticides and miticides.

12 Claims, No Drawings

PHOSPHONODITHIOYLACETYL PHENYL AMINOACID ETHYL ESTERS

BACKGROUND OF THE INVENTION

This invention relates to novel compounds having the structural formula

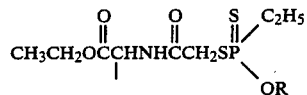

wherein R is lower alkyl having from 1 to 6 carbon atoms and preferably 2 to 4 carbon atoms. Examples of lower alkyl groups are methyl, ethyl, n-propyl, isopropyl, n-butyl, sec-butyl, i-butyl, and n-amyl.

This invention also relates to a method of controlling or combatting insects or mites by applying an insecticidally or miticidally effective amount of a compound as defined herein to the insect or the habitat thereof, or to a locus at which insecticidal or miticidal protection is desired.

This invention also relates to insecticidal or miticidal compositions of matter comprising an insecticidally or miticidally effective amount of a compound as defined herein with an insecticidally or miticidally suitable diluent or carrier.

DESCRIPTION OF THE INVENTION

The novel compounds that are useful in the practice of this invention are phosphonodithioylacetyl phenyl aminoacid ethyl esters having the following structural formula

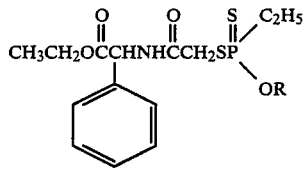

wherein R is lower alkyl having from 1 to 6 carbon atoms and preferably 2 to 4 carbon atoms.

These compounds are useful as insecticides and miticides alone or when compounded with carriers or other active ingredients.

The novel compounds of this invention can be prepared by the following general procedure:

1. Preparation of an aminoacid ester

An aminoacid is suspended in an excess of the alcohol from which the ester is to be prepared and gaseous hydrogen chloride is passed into the mixture at 25°–65° C. An excess of hydrogen chloride of from 3 to 4–5 times the molar amount of aminoacid is used. The product, the aminoacid ester hydrochloride, can be used directly in step 2 or may optionally be converted to the free ester of reaction with ammonium hydroxide.

2. Preparation of a chloroacetylaminoacid ester

The ester prepared in step 1 is reacted with chloroacetylchloride at a temperature of from about −10° to +10° C. in a suitable solvent in the presence of a suitable base to produce the corresponding chloroacetylaminoacid ester. Solvents useful in this reaction include water, dichloromethane, and dichloroethane. Suitable bases include sodium bicarbonate, sodium carbonate, potassium carbonate, and sodium hydroxide. If the aminoacid is used in the form of its hydrochloride, a two-fold excess of base must be used.

3. Preparation of alkyl-O-alkylphosphonodithioylaminoacid ester

The chloroacetylaminoacid ester prepared in step 2 is reacted with an alkyl-O-alkyldithiophosphate or salt thereof at a temperature below 25° C. in a suitable solvent in the presence of a suitable base to produce the corresponding alkyl-O-alkylphosphonodithioylaminoacid ester. Suitable solvents include tetrahydrofuran, dioxane, dichloromethane and dichloroethane. Suitable bases include triethylamine and pyridine. When the salt form of the dithiophosphate is used in the reaction the organic base is not required.

The following examples demonstrate preparation and testing of selected compounds of this invention.

EXAMPLE

Preparation of D-ethyl-O-ethylphosphonodithioylacetyl α-phenylglycine, ethyl ester In a reaction flask, 3.8 grams (g) (0.015 ml) of D-chloroacetyl-α-phenylglycine ethyl ester and 2.9 g (0.017 mole) of ethyl-O-ethyldithiophosphate in 35 milliliters (ml) tetrahydrofuran were mixed and cooled to 15° C. in an ice bath. Triethylamine (1.7 g, 0.01 mole) was added at a temperature below 25° C. with cooling. The pH was adjusted to about 7.5 with additional triethylamine and the mixture was stirred for four hours at room temperature. The solvent was then removed under vacuum and the residue was taken up in 75 ml of benzene and washed with two 100 ml portions of dilute salt solution. The benzene solution was then dried over magnesium sulfate, filtered and evaporated to give 5.1 g (87.9% yield) of an amber viscous liquid having an $n_D^{30} = 1.5523$. The product was identified by nuclear magnetic resonance (NMR) spectroscopy as the title compound.

The following is a table of certain selected compounds that are useful in the practice of this invention. These compounds are preparable according to the general and specific procedure described herein. Compound numbers are assigned to each compound and are used throughout the remainder of this application.

TABLE I

| Compound No. | R | $n_D^{30}$ |
|---|---|---|
| 1 | —$C_2H_5$ | 1.5523 |
| 2 | —$C_3H_7$—i | 1.5461 |
| 3 | —$C_4H_9$—i | 1.5444 |

The structures of these compounds were confirmed by infrared (IR) and/or nuclear magnetic resonance (NMR) spectral analyses.

Insecticidal Evaluation

The compounds in the above Table I were tested for insecticidal acitvity against the following insects:
Housefly [*Musca domestica* (Linn.)]
German Cockroach [*Blatella germanica* (Linn.)]
Lygus Bug [*Lygus hesperus* (Knight)]

Black Bean Aphid [*Aphis fabae* (Scop.)]
Green Peach Aphid [*Myzus persicae* (Sulzer)]
Saltmarsh Caterpillar [*Estigmene acrea* (Drury)]
Tobacco Budworm [*Heliothis virescens* (Fabricius)]
Cabbage Looper [*Trichoplusia ni* (Hubner)]
Southern House Mosquito [*Culex pipiens quinquefasciatus* (Say)]

The following testing procedures were used for this evaluation.

Housefly [*Musca domestica*]:

Test compounds were diluted in acetone and aliquots pipetted onto the bottom of 55×15 mm aluminum dishes. To insure even spreading of the chemical on the bottom of the dishes, 1 ml of acetone containing 0.02% peanut oil was also added to each dish. After all solvents had evaporated, the dishes were placed in circular cardboard cages containing 25 female houseflies, one to two days old. The cages were covered on the bottom with cellophane and on the top with tulle netting, and each contained a sugar-water saturated cotton plug for maintenance of the flies. Mortality was recorded after 48 hours. Test levels ranged from 100 ug/25 female houseflies down to that at which approximately 50% mortality occurred. The LD-50 values are expressed below in Table II under the heading "HF", in terms of ug of the test compound per 25 female houseflies.

German Cockroach [*Blatella germanica* (Linn.)]:

Test compounds were diluted in a 50-50 acetone-water solution. Two cc of the solution was sprayed through a hand spray gun into circular cardboard cages containing 10 one-month old German cockroach nymphs. The test cages were covered on the bottom with cellophane and on the top with tulle netting. Percent mortality was recorded 4 days later. Test concentrations ranged from 0.1% down to that at which approximately 50% mortality occurred. LD-50 values are expressed below in Table II under the heading "GR" in terms of percent of the test compound in the sprayed solution.

Lygus Bug [*Lygus hesperus* (Knight)]:

Test compounds were diluted in a 50-50 acetone-water solution. Two cc of the solution were sprayed through a hand spray gun into circular cardboard cages containing 1 green bean pod and 10 adult lygus bugs. The test cages were covered on the bottom with cellophane and on the top with tulle netting. Percent mortality was recorded 48 hours later. Test concentrations ranged from 0.05% down to that at which approximately 50% mortality occurred. LD-50 values are expressed below in Table II under the heading "LB" in terms of percent of the test compound in the sprayed solution.

Black Bean Aphid [*Aphis fabae* (Scop.)]:

Nasturtium plants (Tropaeolum sp.) approximately 5 cm tall, were transplanted into sandy loam soil in 3-inch clay pots and infested with 25-50 black bean aphids of mixed ages. Twenty-four hours later they were sprayed to the point of runoff with 50-50 acetone-water solutions of the test chemicals. Treated plants were held in the greenhouse and mortality was recorded after 48 hours. Test concentrations ranged from 0.05% down to that at which 50% mortality occurred. LD-50 values are expressed below in Table II under the heading "BA" in terms of percent of the test compound in the sprayed solution.

Green Peach Aphid [*Myzus persicae* (Sulzer)]:

Radish plants (*Rhaphanus sativus*), approximately 2 cm tall, were transplanted into sandy loam soil in 3-inch clay pots and infested with 25-50 green peach aphids of mixed ages. Twenty-four hours later they were sprayed to the point of run-off with 50-50 acetone-water solutions of the test chemicals. Treated plants were held in the greenhouse and mortality was recorded after 48 hours. Test concentrations ranged from 0.05% down to that at which 50% mortality occurred. LD-50 values are expressed below in Table II under the heading "GPA" in terms of percent of the test compound in the sprayed solution.

Saltmarsh Caterpillar [*Estigmene acrea* (Drury)]:

Test compounds were diluted in a 50-50 acetone-water solution. Sections of curly dock (*Rumex crispus*) leaves, approximately 1×1.5 inches, were immersed in the test solution for 2-3 seconds and placed on a wire screen to dry. The dried leaves were placed in petri dishes containing a moistened piece of filter paper and infested with 5 second-instar saltmarsh larvae. Mortality of the larvae was recorded 48 hours later, and a piece of synthetic medium was added to dishes containing survivors. These were then held for 5 additional days to observe for any delayed effects of the test chemicals.

Test concentrations ranged from 0.05% down to that at which approximately 50% mortality occurred. LD-50 values are expressed below in Table II under the heading "SMC" in terms of percent of the test compound in the solution.

Cabbage Looper [*Trichoplusia ni* (Hubner)]:

Test compounds were diluted in a 50-50 acetone-water solution. Cotyledons of hyzini squash (*Calabacita abobrinha*), approximately 1×1.5 inches, were immersed in the test solutions for 2-3 seconds and placed on a wire screen to dry. The dried leaves were placed in petri dishes containing a moistened piece of filter paper and infested with five second-instar cabbage looper larvae. Mortality of the larvae was recorded 48 hours later, and a piece of synthetic media added to dishes containing survivors. These were then held for five additional days to observe for any delayed effects of the test chemicals.

Test concentrations ranged from 0.05% to that at which approximately 50% mortality occurred. LD-50 values are expressed below in Table II under the heading "CL" in terms of percent of the test compound in this solution.

Tobacco budworm [*Heliothis virescens* (Fabricius)]:

Test compounds were diluted in a 50-50 acetone-water solution. Sections of Romanine lettuce (*Latuca sativa*) leaves, approximately 1×1.5 inches, were immersed in the test solutions for 2-3 seconds and placed on a wire screen to dry. The dried leaves were placed in petri dishes containing a moistened piece of filter paper and infested with five second-instar tobacco budworm larvae. Mortality of the larvae was recorded 48 hours later, and a piece of synthetic media added to dishes containing survivors. These were then held for five additional days to observe for any delayed effects of the test chemicals.

Test concentrations ranged from 0.05% to that at which approximately 50% mortality occurred. LD-50 values are expressed below in Table II under the heading "TBW" in terms of percent of the test compound in the solution.

Southern House Mosquito Larvae [*Culex pipiens quinquefasciatus* (Say)]:

Insecticidal activity was determined using third instar larvae of the mosquito *Culex pipiens quinquefasciatus*.

Ten larvae were placed in a six ounce paper cup containing 100 milliliters of an aqueous solution of the test chemical. The treated larvae were stored at 70° F., and 48 hours later the mortality was recorded. Test concentrations ranged from 1.0 ppm down to that at which approximately 50% mortality occurred. LD-50 values are expressed below in Table II under the heading "MOS" in terms of parts per million (ppm) of the test compound in the solution.

Acaricidal Evaluation Test

The two-spotted mite (2SM), *Tetranychus urticae* (Koch), was employed in tests for miticides. The test procedure was as follows:

Pinto bean plants (Phaseolus sp.) approximately 10 cm tall, were transplanted into sandy loam soil in 3-inch clay pots and thoroughly infested with two-spotted mites of mixed ages and sexes. Twenty-four hours later the infested plants were inverted and dipped for 2-3 seconds in 50-50 acetone-water solutions of the test chemicals. Treated plants were held in the greenhouse, and 7 days later mortality was determined for both adult mites and the nymphs hatching from eggs which were on the plants at the time of treatment. Test concentrations ranged from 0.05% down to that at which 50% mortality occurred. LD-50 values are expressed below in Table II under the headings "2SM-PE" (i.e., post-embryonic) and "2SM-Eggs", in terms of percent concentrations of the test compound in the solution.

TABLE II

| Comp. No. | HF, ug | GR % | LB % | BA % | GPA % | SMC % | TBW % | CL % | MOS ppm | PE % | EGGS & |
|---|---|---|---|---|---|---|---|---|---|---|---|
| 1 | >100 | >0.1 | >0.05 | 0.008 | 0.008 | 0.03 | >0.05 | >0.05 | >1 | 0.05 | <0.05 |
| 2 | 100 | — | — | 0.008 | 0.03 | — | >0.05 | — | >1 | <0.05 | <0.05 |
| 3 | 100 | >0.1 | >0.05 | 0.005 | 0.002 | <0.01 | >0.05 | >0.05 | 0.8 | >0.05 | >0.05 |

In practice, a pure compound can be used as an insecticide. However, in general, the compounds are first formulated with one or more inert carriers or diluents suitable for insecticidal use, before being applied.

The compositions or formulations, including a compound as described herein, may take and be used in any one of a number of solid or liquid forms. Examples of solid forms are dusts, granules, tablets, powders, and the like. Examples of liquid forms are emulsions, solutions, suspensions, emulsifiable concentrates, flowables, and pastes. Such compositions may contain, in addition to the active compound or compounds, various carriers or diluents; surface active agents (wetting agents, dispersing agents and/or emulsifying agents); solvents (water or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcium carbonate, silica, kieselguhr, clay, etc.; ground synthetic minerals such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders, flowables and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons with an emulsifying agent. To obtain suspensions or emulsions in water, wetting agents are also added.

It is possible to use highly concentrated liquid compositions containing up to about 95% by weight of the active compound, or even the 100% active compound alone, when applying the compound in the form of a finely divided liquid by use of various atomizing equipment, for example by airplane crop spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: wettable powders, flowables and pastes,—20 to 90% active compound; oil suspensions, emulsions, solutions and emulsifiable concentrates—5 to 90% active compound; aqueous suspensions—10 to 50% active compound; dusts and powders—1 to 25% active compound; granules and pellets—1 to 20% active compound.

The rate of application of the active compound to a locus to be controlled will depend on the nature of the insects to be controlled and will vary from about 0.05 to about 50 pounds per acre (about 0.06 to about 56 kg/ha).

In addition to the active compound and the various agents utilized in preparing compositions and formulations mentioned above, such compositions may also contain one or more other active compounds of the type mentioned herein as well as other active pesticidal agents, such as herbicides, fungicides, insecticides, acaricides, nematocides, bactericides, and plant growth regulators. Such compositions may also contain soil disinfectants or fumigants and may further contain fertilizers, thus making it possible to provide multi-purpose compositions containing one or more of the compounds described herein as well as, optionally, other pesticides and also fertilizers, all intended and formulated for use at the same locus.

Control of insect pests is accomplished by applying a composition containing an insecticidally effective amount of an active compound as described herein, to the insect, to a locus at which insecticidal control is desired, or to food sources (including seeds) on which the insects feed. For use in the last mentioned manner, it is preferable to utilize a compound which is not volatile. Thus, control may be achieved by direct application of the active compounds to the insects and indirectly by application of the compounds to a locus to be protected (such as crop lands, grass ranges, and forests), to a source of food for insects or to other insect habitats (for example, breeding or swarming areas). The rates of application of the active compound, and the concentration applied, will vary according to whether the compound or composition is being directly applied to the insect or indirectly, to a locus, food or habitat. In the latter case the rate of the application, depending on the nature of the insect or insects to be controlled, and the plant environment, will generally vary from about 0.01 to about 100 pounds per acre (about 0.112 to about 1120 kg/ha.)

What is claimed is:

1. A method for controlling insects comprising applying to the insects, the habitat thereof, or a locus where protection is desired, an insecticidally effective amount of a compound having the formula

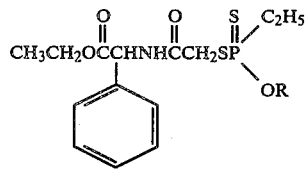

wherein R is lower alkyl having from 1 to 6 carbon atoms.

2. The method of claim 1 wherein R is -$C_2H_5$.

3. The method of claim 1 wherein R is -$C_3H_7$-i.
4. The method of claim 1 wherein R is -$C_4H_9$-i.
5. A compound having the structural formula

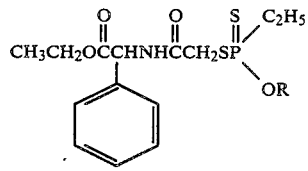

wherein R is lower alkyl having from 1 to 6 carbon atoms.

6. The compound of claim 5 wherein R is -$C_2H_5$.
7. The compound of claim 5 wherein R is -$C_3H_7$-i.
8. The compound of claim 5 wherein R is -$C_4H_9$-i.
9. A composition of matter comprising
   (a) an insecticidally effective amount of a compound having the structural formula

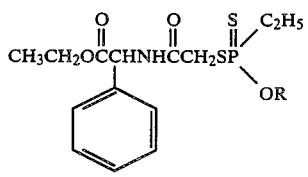

wherein R is lower alkyl having from 1 to 6 carbon atoms; and
   (b) an insecticidally suitable inert carrier or diluent.

10. The composition of claim 9 wherein R is -$C_2H_5$.
11. The composition of claim 9 wherein R is -$C_3H_7$-i.
12. The composition of claim 9 wherein R is -$C_4H_9$-i.

* * * * *